(12) United States Patent
Sekiguchi et al.

(10) Patent No.: US 8,007,104 B2
(45) Date of Patent: Aug. 30, 2011

(54) FUNDUS CAMERA

(75) Inventors: Kyoji Sekiguchi, Utsunomiya (JP); Shigeaki Ono, Tokyo (JP); Masao Shikaumi, Tokyo (JP); Motoya Takai, Nagareyama (JP); Toshifumi Masaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/774,547

(22) Filed: May 5, 2010

(65) Prior Publication Data

US 2010/0283970 A1    Nov. 11, 2010

(30) Foreign Application Priority Data

May 8, 2009   (JP) .................................. 2009-113451

(51) Int. Cl.
*A61B 3/14* (2006.01)
(52) U.S. Cl. ...................................................... 351/206
(58) Field of Classification Search .................. 351/206, 351/205, 221, 246, 200
See application file for complete search history.

(56) References Cited

U.S. PATENT DOCUMENTS 7,641,338 B2 *   1/2010  Fukuma et al. ............... 351/206
7,828,437 B2 * 11/2010  Kikawa et al. ................ 351/206

FOREIGN PATENT DOCUMENTS

| JP | 5-199998 A | 8/1993 |
|----|-----------|--------|
| JP | 4138101 B2 | 8/2008 |

\* cited by examiner

*Primary Examiner* — Hung X Dang
(74) *Attorney, Agent, or Firm* — Canon U.S.A., Inc., IP Division

(57) ABSTRACT

A fundus camera includes an observation photographing unit having a focusing lens to perform focusing of an imaging unit on a fundus of a subject's eye, a lens driving unit configured to drive the focusing lens in an optical axis direction, and a focusing control unit configured to calculate a focusing evaluation value based on image information of a predetermined area of a fundus image captured by the observation photographing unit, and drive the focusing lens based on the focusing evaluation value, thereby performing focusing, wherein the focusing control unit moves the focusing lens from a previous photographing position of the focusing lens by a predetermined moving amount, and then performs the focusing.

5 Claims, 10 Drawing Sheets

FUNDUS CAMERA

BACKGROUND OF THE INVENTION

1. Field of the Invention

The present invention relates to a fundus camera that includes an automatic focusing unit.

2. Description of the Related Art

There is conventionally known a fundus camera that includes an illumination optical system configured to illuminate a fundus of subject's eye, a photographic optical system configured to photograph the fundus, an observation optical system configured to observe the fundus, and a focusing optical system configured to focus on the fundus. Photographing the fundus necessitates complex work and experience such as performing alignment with a pupil of subject's eye, working distance adjustment, focusing, and line-of-sight guiding, and paying attention to rising or blinking of an eyelid.

Thus, there is used a fundus camera that facilitates fundus photographing by automating focusing. Automatic focusing systems are largely classified into two types: a detection method of projecting a focusing index to the fundus and capturing and processing its index image, and a method of detecting a blur of a captured fundus image without using any focusing index.

Japanese Patent No. 4138101 discusses a fundus camera in which, in a focusing index projection system, eye refractive power of subject's eye is input before fundus photographing, a focusing lens is moved to a suitable position, and then focusing is started. This arrangement is for the purpose of solving a problem of a focusing time delay caused by a longer period of moving time of the focusing lens when refractive power is large.

In the case of the fundus camera that performs focusing control by the fundus image blur detection method, if the focusing lens is roughly moved to an eye refractive power position of subject's eye beforehand, the focusing lens is moved to the vicinity of a vertex of a focusing evaluation value curve.

However, a shape of the focusing evaluation value curve obtained from the fundus image is not sharp. Thus, even when after the focusing lens is moved to the vicinity of the vertex, the focusing evaluation value is acquired to calculate an in-focus position, it is difficult to determine in which side the peak of the mountain exists. At least, a mountain of the focusing evaluation value curve is scanned nearly from a mountainside to understand an overall shape of the mountain, and then the vertex is found. Otherwise, no accurate focusing result can be obtained.

Thus, in the conventional fundus camera, the focusing lens is first moved to a −end side of a moving range, and then scanning is started to acquire a focusing evaluation value in a +end direction. After detection of a mountain peak of the focusing evaluation value, the scanning is stopped when the focusing evaluation value becomes equal to or less than a given setting value. Then, the focusing lens is moved back to a peak position of the focusing evaluation value to perform photographing.

In FIG. 10, a horizontal axis represents a moving range of the focusing lens, and a +end indicates a limit position of a plus diopter, and a −end indicates a limit position of a minus diopter. A vertical axis (plus side) represents a focusing evaluation value obtained by adding a value of a high-frequency component obtained in a predetermined area of the fundus image. Contrast is higher near the in-focus position, and then the focusing evaluation value is larger.

A focusing evaluation value curve of FIG. 10 is an example of a focusing evaluation value when the focusing lens is scanned within the entire moving range. Actually, only a curve of a scanned range is obtained. A lower side of the vertical axis of FIG. 10 indicates a sequence of focusing lens movement and focusing evaluation value scanning on a time axis.

A solid line Mx indicates a case where only movement of the focusing lens is performed, and a broken line Sx indicates a case where scanning for focusing evaluation value acquisition is performed, x indicating order. The graph also illustrates a start position 301 of focusing lens control, and a focusing end position 301. Normally, photographing is performed in the focusing end position 302.

In this example, the focusing lens moves from the position 301 to the −end, starts scanning S1 to acquire a focusing value from M1 in a +direction, detects a peak of a focusing evaluation value curve on the way, stops when a focusing evaluation value becomes equal to or less than a threshold value L0, and moves (M2) to perform photographing at a peak position. A moving speed of the focusing lens is, in an operation Sx that is accompanied by focusing evaluation value acquisition, greatly lower than that of movement Mx where only movement is performed.

However, such a fundus camera is based on the premise that eye refractive power of subject's eye is known beforehand, and a unit for inputting the eye refractive power is necessary. Consequently, the number of operation units increases, causing a cost increase. In the case of the fundus camera that performs focusing control by the blur detection focusing method, scanning for a focusing evaluation value is performed after moving to the −end position (or +end) of the focusing range, and hence it takes time to focus.

SUMMARY OF THE INVENTION

The present invention relates to a fundus camera capable of performing automatic focusing within a short period of time by using a simple blur detection focusing method in an optical system configuration.

According to an aspect of the present invention, a fundus camera includes an observation photographing unit having a focusing lens to perform focusing of an imaging unit on a fundus of a subject's eye, a lens driving unit configured to drive the focusing lens in an optical axis direction, and a focusing control unit configured to calculate a focusing evaluation value based on image information of a predetermined area of a fundus image captured by the observation photographing unit, and drive the focusing lens based on the focusing evaluation value, thereby performing focusing, wherein the focusing control unit moves the focusing lens from a previous photographing position of the focusing lens by a predetermined moving amount, and then performs the focusing.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

An exemplary embodiment of the present invention will be described in detail referring to FIGS. 1 to 9 below.

Figure 1:
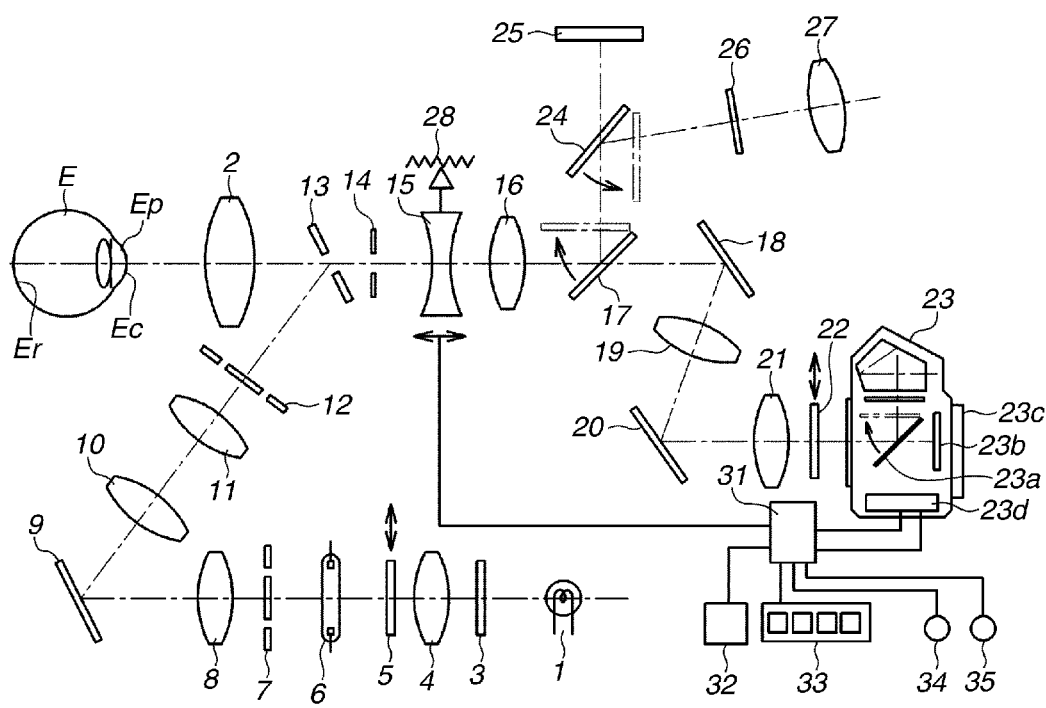
FIG. 1 illustrates a configuration of a fundus camera according to an exemplary embodiment of the present invention.

FIG. 1 illustrates a configuration of a fundus camera according to the exemplary embodiment of the present invention. In an illumination optical system from a halogen lamp 1 serving as a fundus observation light source to an objective lens 2 arranged before subject's eye E, there are laid out the halogen lamp 1 that is an observation light source, a diffusion plate 3, a condenser lens 4, and a visible-light cut filter 5. There are sequentially laid out a flash light source 6 serving as a photographing light source roughly conjugate with respect to a pupil Ep of subject's eye E, a ring slit 7, a condenser lens 8, a fixed mirror 9, relay lenses 10 and 11, a cornea baffle 12, and a perforated mirror 13.

After the perforated mirror 13, there are laid out a photographic diaphragm 14, a focusing lens 15, an imaging lens 16, a flip-up mirror 17 constituted of a dichroic mirror for reflecting visible light while transmitting infrared light, and a fixed mirror 18. In a reflection direction of the fixed mirror 18, a relay lens 19, a mirror 20, a relay lens 21, an infrared-light cut filter 22 inserted into an optical path during photographing, and a digital camera 23 for performing observation photographing of a fundus image are sequentially laid out to constitute an observation photographic optical system.

In a reflection optical path of the flip-up mirror 17, a movable mirror 24 and an internal fixation lamp 25 are arranged. In a reflection direction of the movable mirror 24, a field stop 26 and an eyepiece lens 27 are laid out to constitute a finder optical system.

The digital camera 23 is attached to a fundus camera body via a detachable mount. The digital camera 23 incorporates a quick return mirror 23a, a CMOS area sensor 23b, an LCD monitor 23c, and a processing circuit 23d.

The CMOS area sensor 23b includes a RGB filter configured to transmit a near infrared region. The CMOS area sensor 23b has sensitivity to visible and infrared regions, and can capture a moving image and a still image. During moving image capturing, a gain of an amplifier of the CMOS area sensor 23b is set to high sensitivity, and the processing circuit 23d performs thinning so as to match resolution of the LCD monitor 23c. As a result, a moving image is displayed on the LCD monitor 23c with lowered resolution.

The focusing lens 15 includes a potentiometer 28 configured to detect its position. The processing circuit 23d of the digital camera 23 is connected to a control unit 31. A storage unit 32, a shooting mode switch 33, a left/right eye detection unit 34, and a shooting switch 35 are connected to the control unit 31. An output of the control unit 31 is connected to the focusing lens 15 to drive the focusing lens 15.

The control unit 31 controls insertion/ejection of the flip-up mirror 17, the movable mirror 24, the filters 5 and 22, positioning of the focusing lens 15, and communication with the digital camera 23. The control unit 31 is connected to the shooting switch 35, the left/right eye detection unit 34 configured to detect a direction of an eye to be photographed, the shooting mode switch 33, and the storage unit 32 configured to store a photographing position distribution for each shooting mode or photographing in a form of a database for each date and week.

When photographing a fundus Er of subject's eye E, the flash light source 6 emits light to photograph a still image. In this case, the gain of the amplifier of the CMOS area sensor 23b is returned normal to increase S/N, and image data having resolution of all pixels of the CMOS area sensor 23b is subjected to development processing at the processing circuit 23d, and saved in a file format designated in a storage medium (not illustrated).

Figure 2:
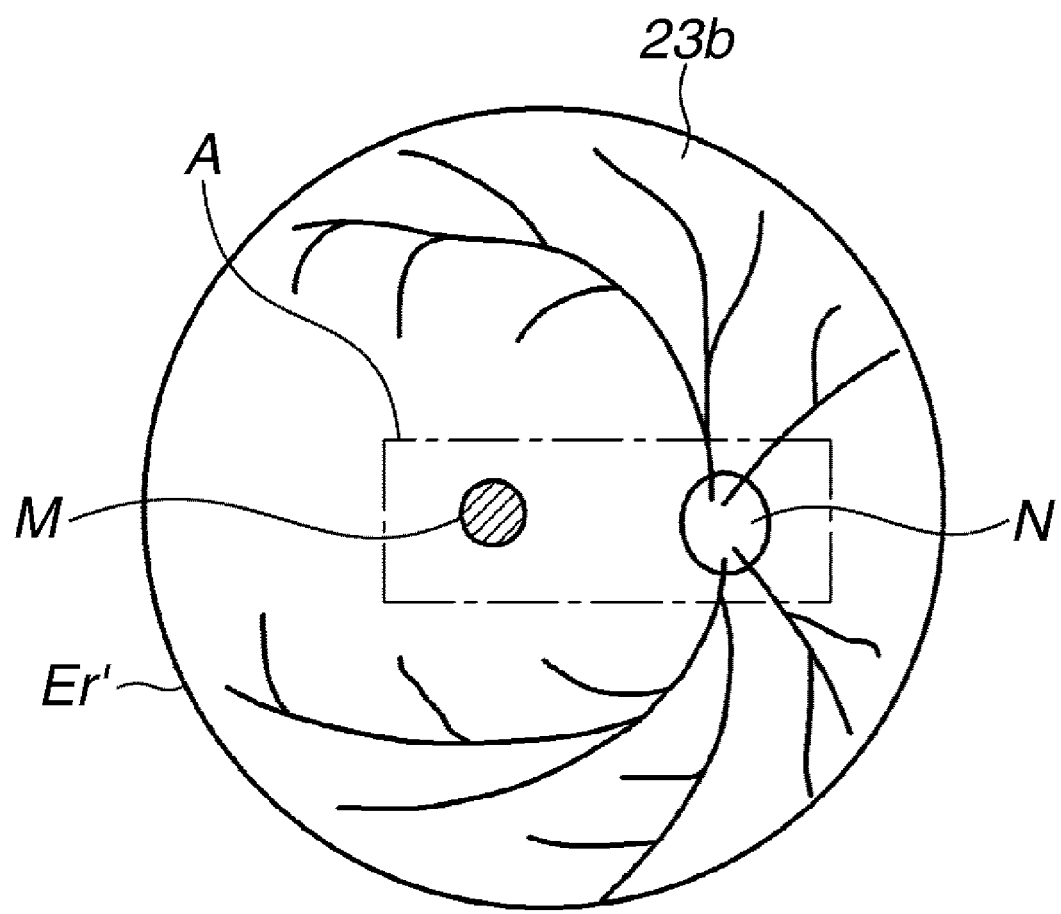
FIG. 2 illustrates an area for calculating a focusing evaluation value.

FIG. 2 illustrates an area for calculating contrast of a fundus image. A fundus image Er' is formed on the CMOS area sensor 23b. An area A including a macular area M and an optic disk area N indicates a range for calculating contrast. The processing circuit 23d adds a signal having band limited to a high-frequency component of image information of the area A from a moving image of the fundus image to be photographed, and outputs a focusing evaluation value indicating a level of an in-focus state.

A focusing evaluation value of a predetermined area is acquired while moving the focusing lens 15. A focusing evaluation value at each point within a moving range is complemented by a spline curve, and a peak position of a focusing evaluation curve is calculated to obtain an in-focus position. The control unit 31 moves the focusing lens 15 based on a result of this calculation. While loaded on the fundus camera, the quick return mirror 23a in the digital camera 23 is held in a flipped-up state.

When there is no operation input for a given period of time, the control unit 31 moves the focusing lens 15 in an optical axis direction to a rough center position (0 diopter) of the moving range by a lens driving unit. In order to maintain focusing accuracy by eliminating an influence of backlash of the driving unit of the focusing lens 15, the control unit 31 controls the focusing lens 15 to stop by moving thereof from the same direction to perform photographing.

In the present exemplary embodiment, a moving direction is from + to −, and a focusing evaluation value scanning direction is from − to +. However, directions may be reverse. In the case of performing focusing evaluation value scanning, two methods are available: a method for acquiring a focusing evaluation value by setting a moving speed of the focusing lens 15 low and moving, and a method for acquiring a focusing evaluation value after the focusing lens 15 stopped. In the former method, the moving speed must be reduced so that a moving distance can be equal to or less than focusing accuracy during acquisition of the focusing evaluation value. In the latter method, while the moving speed is increased, but sudden acceleration or sudden stop can occur, thereby generating vibrations. Thus, in both of the methods, the focusing evaluation value scanning speed becomes lower as compared with the case where only movement is performed.

During fundus observation, white light emitted from the halogen lamp 1 is transmitted through the visible-light cut filter 5 to illuminate the fundus Er with infrared light. During photographing, the halogen lamp 1 is turned OFF, and the flash light source 6 emits light to illuminate the fundus Er.

A photographing position distribution of a one-month period is read from the database according to a shooting mode, and the focusing lens 15 can be moved to a corresponding position. When a casing (not illustrated) including the optical system of the fundus camera is moved according to a left eye or a right eye of subject's eye E, the left/right eye detection unit 34 is turned ON/OFF to enable detection of a left/right eye to be photographed.

With the above-mentioned configuration, mydriatic photographing or non-mydriatic photographing can be selected by the shooting mode switch 33. When the mydriatic shooting mode is selected, the visible-light cut filter 5 is retracted out of the optical path, while the infrared-light cut filter 22 is inserted into the optical path.

In setting for performing automatic focusing, the flip-up mirror 17 retracts from the optical path. Visible light emitted from the halogen lamp 1 is passed through the ring slit 7 and the condenser lens 8 to be reflected by the fixed mirror 9, and reflected at the peripheral part of the perforated mirror 13. The visible light is passed through the objective lens 2 and the pupil Ep, and then illuminates the fundus Er.

The reflected light from the fundus Er passes through the center of the pupil Ep to be transmitted through the objective lens 2 and a hole of the perforated mirror 13, and passes through the photographic diaphragm 14 and the focusing lens 15 to be reflected by the fixed mirrors 18 and 20. The light is further transmitted through the infrared-light cut filter 22 to form an image on the CMOS area sensor 23b of the digital camera 23.

When the shooting mode switch 33 selects the non-mydriatic shooting mode, the visible-light cut filter 5 is inserted into the optical path, and the flip-up mirror 17 enters the optical path. The movable mirror 24 retracts in a broken line direction, and the infrared-light cut filter 22 retracts out of the optical path. A light flux emitted from the halogen lamp 1 has its visible light cut by the visible-light cut filter 5 to become near-infrared light. The near-infrared light is reflected at peripheral part of the perforated mirror 13, and transmitted through the objective lens 2 to illuminate the fundus Er.

A fundus image formed by the near-infrared light reflected on the fundus Er passes through the objective lens 2 and the hole of the perforated mirror 13, and then passes through the focusing lens 15 and the flip-up mirror 17 to be reflected by the fixed mirrors 18 and 20, thereby forming an image on the CMOS area sensor 23b. A fundus observation image generated by the CMOS area sensor 23b is displayed as a moving image on the LCD monitor 23c. Hence, an examiner performs an alignment operation by using an operation stick.

In the non-mydriatic mode, a visible light flux from the internal fixation lamp 25 proceeds straight ahead because of the retraction of the movable mirror 24 from the optical path. The light flux is reflected by the flip-up mirror 17, and transmitted through the focusing lens 15, the hole of the perforated mirror 13, and the objective lens 12 to be projected to subject's eye E. Thus, subject's eye E is directed to a light source image by the internal fixation lamp 25, and the examiner adjusts, using a switch (not illustrated), a light emitting position of the internal fixation lamp 25 to adjust a direction of the fundus Er.

In the mydriatic mode, an external fixation lamp (not illustrated) installed outside is gazed by an eye different from the eye to be photographed to adjust a position of the fundus Er. When the finder optical system is used in the mydriatic mode, the flip-up mirror 17 and the movable mirror 24 are inserted into the optical path by an operation of a switch (not illustrated).

The visible light reflected on the fundus Er is reflected by the flip-up mirror 17 and the movable mirror 24 to be guided to the eyepiece lens 27 of the finder optical system. The light flux from the fundus Er is not incident on the digital camera 23, and hence no automatic focusing control is performed. The examiner performs focusing by rotating a knob (not illustrated) to move the focusing lens 15.

After completion of the alignment with the fundus Er, when the shooting switch 35 is pressed half, the control unit 31 moves the focusing lens 15 by a predetermined moving amount in a minus diopter direction (−direction). Then, scanning accompanied by acquisition of a focusing evaluation value in a plus diopter direction (+direction) is started. This predetermined moving amount is set according to the shooting mode.

After completion of the focusing, the examiner is notified of the completion by a display or a sound. When the shooting switch 35 is fully pressed, the flip-up mirror 17 is flipped up in the case of using the finder in the non-mydriatic mode or the mydriatic mode. In the non-mydriatic mode, the infrared-light cut filter 22 is inserted into the optical path, and the flash light source 6 emits light, thereby performing photographing.

Concerning a peak position of a focusing evaluation value acquired in the non-mydriatic mode, as compared with the case of the mydriatic mode where the fundus Er is illuminated by visible light, an in-focus position is slightly deeper than a retina of the fundus Er. Hence, the focusing lens 15 is moved to perform correction before photographing light is emitted.

Each of FIGS. 3 to 6 illustrates an operation of the focusing lens 15 when the same subject's eye E is continuously photographed. A horizontal axis represents a movable range of the focusing lens 15, and a right side thereof indicates a + end, and a left side thereof indicates a −end. A+ side of a vertical axis indicates a focusing evaluation value, and a − side indicates a time axis when the focusing lens 15 is driven.

The graph illustrates a previous position 300 of the focusing lens 15, a start position 301 of a driving sequence of the focusing lens 15, and an end position 302 of the driving sequence of the focusing lens 15. A solid line indicates that only movement of the focusing lens 15 is performed, and a broken line indicates focusing evaluation value scanning where the focusing lens 15 is moved while acquiring a focusing evaluation value.

A threshold value L1 is a level of a focusing evaluation value to determine a stop position or a return position of movement of the focusing lens 15. A focusing evaluation value curve illustrates a case where the focusing lens 15 performs full-range scanning. In practice, focusing evaluation values of a range exceeding the threshold value L1 are extracted, and hence only this curve is obtained. The focusing lens 15 is moved only by a predetermined moving amount W set beforehand.

Figure 3:
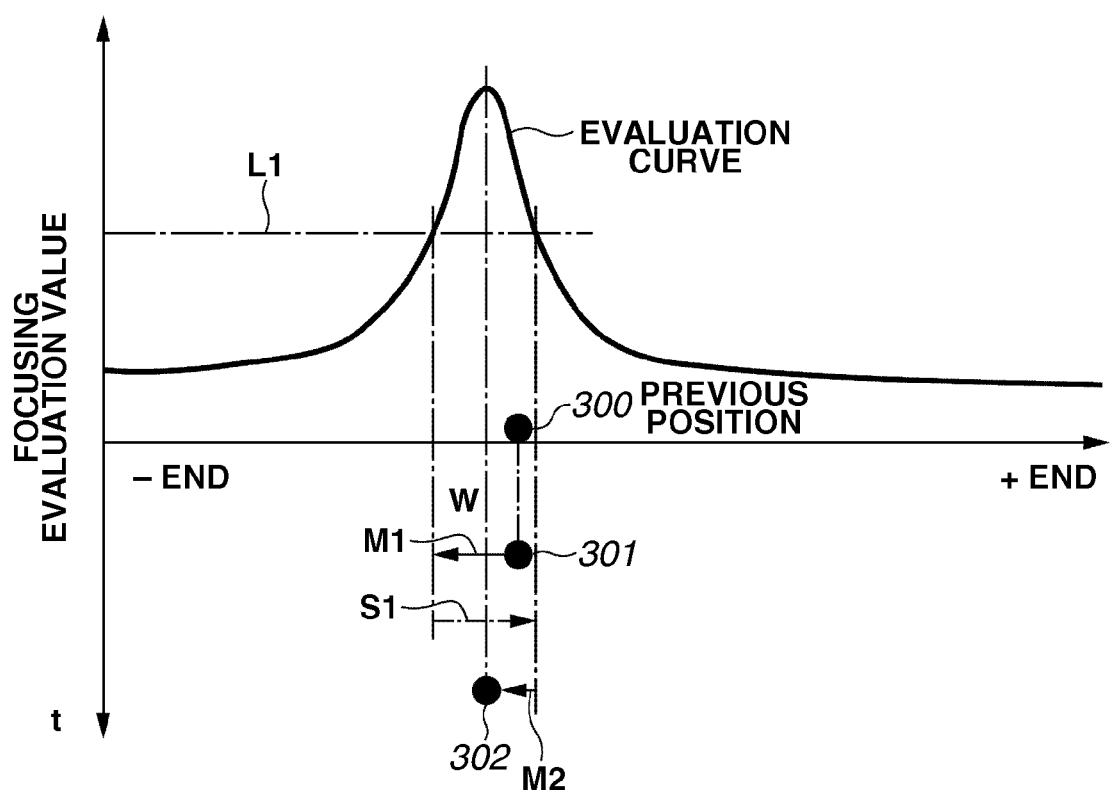
FIG. 3 is a graph illustrating an operation of a focusing lens.

FIG. 3 illustrates an example where the current in-focus position 302 is within a range of the predetermined moving amount W on the − side with respect to the previous position 300. When the shooting switch 35 is pressed half, the focusing lens 15 is moved (M1) by the predetermined moving amount W from the position 301 in a − direction. A focusing evaluation value in this position is set as the threshold value L1, and the moving direction is changed to the + side to start scanning (S1) for focusing evaluation values.

When a focusing evaluation value drops below the threshold value L1, and a peak is detected, the focusing lens 15 is stopped, and moved (M2) in the − direction to a peak position. Thus, focusing is completed, and the examiner recognizes the completion by a display (not illustrated).

Figure 4:
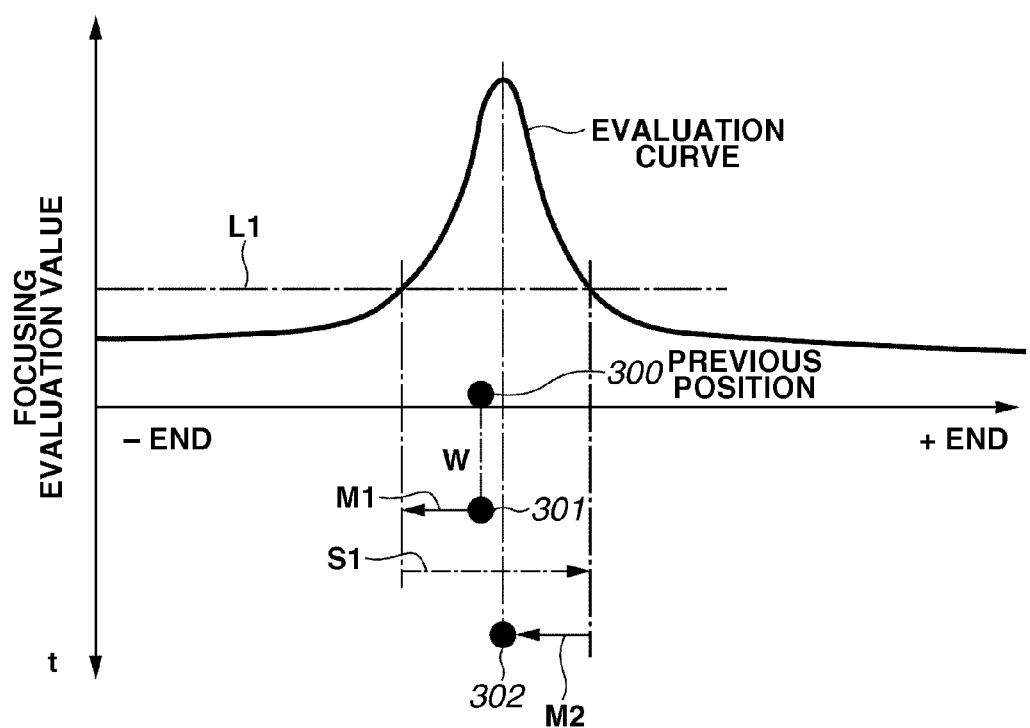
FIG. 4 is a graph illustrating an operation of the focusing lens.

FIG. 4 illustrates an example where the current in-focus position 302 is within a range of the predetermined moving amount W on the + side with respect to the previous position 300. First, the focusing lens 15 is moved (M1) by the predetermined moving amount W from the start position 300 in the − direction. A focusing evaluation value in this position is set as the threshold value L1. Then, the moving direction is changed to the + side to start focusing evaluation value scanning S1.

When the acquired focusing evaluation value is equal to or less than the threshold value L1, and a peak is detected, the focusing lens 15 is stopped, and moved (M2) in the −direction to a peak position. As compared with the case of FIG. 3, while distances of the scanning S1 and the movement M2 are a little longer, other operations are similar.

Figure 5:
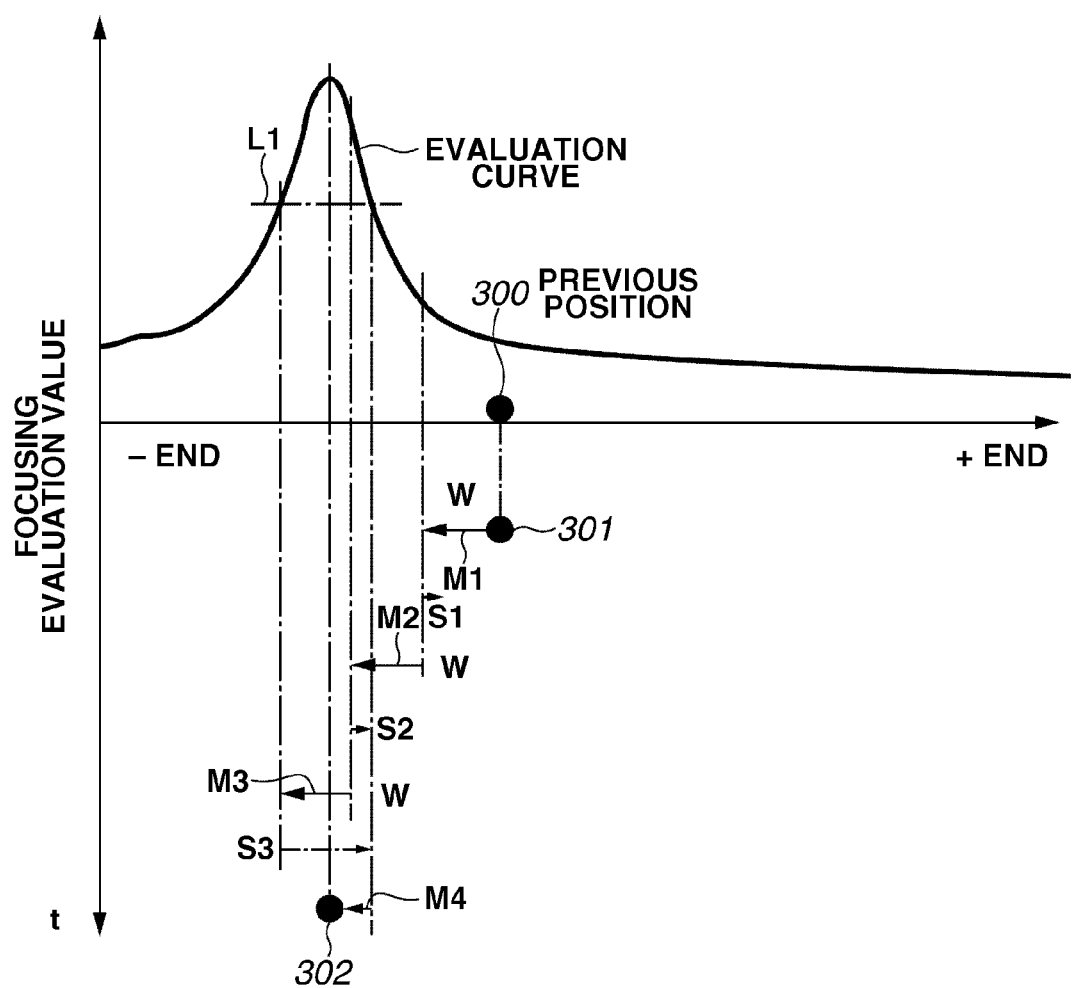
FIG. 5 is a graph illustrating an operation of the focusing lens.

FIG. 5 illustrates an example where the current in-focus position 302 is away from the previous position 300 by more than the predetermined moving amount W on the − side. Normally, when the same eye is photographed, this situation will not occur, it is only limited to a case where there is a large difference in refractive power between left and right eyes. In operation, the focusing lens 15 is moved by W from the start position 301 to the − side to start scanning of a focusing evaluation value toward the + side. However, continuously acquired focusing evaluation values are equal to or less than the threshold value L1, and hence focusing scanning S1 is immediately canceled.

Then, the focusing lens 15 is moved (M2) by W from the position of the first movement, in other words, from the start position 301 to a position 2W in the − direction. Similarly, scanning S2 of focusing evaluation values is started in the + direction. The focusing evaluation values are continuously equal to or less than the threshold value L1, and hence the scanning S2 is canceled. Similarly, the focusing lens 15 is moved to a position 3W on the − side, and the threshold value L1 is updated to start scanning S3. A peak is detected, and a focusing evaluation value drops below the threshold value L1. Thus, the scanning is stopped, and the focusing lens 15 is moved (M4) to the peak position.

Figure 6:
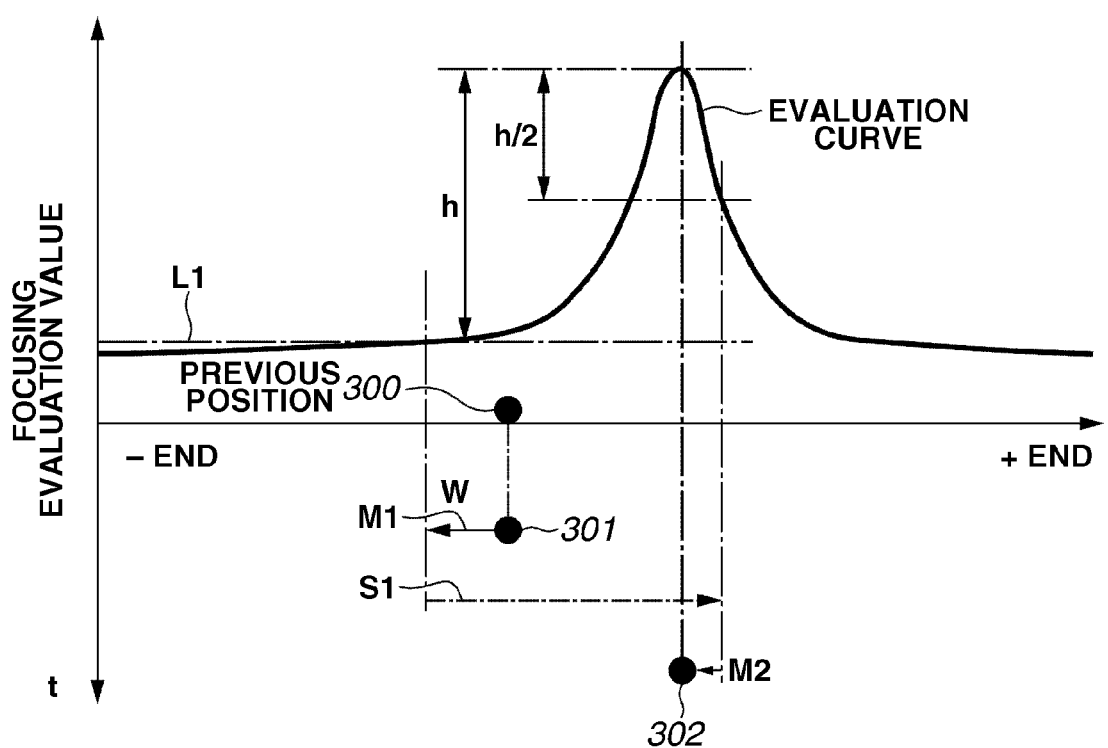
FIG. 6 is a graph illustrating an operation of the focusing lens.

FIG. 6 illustrates an example where the current in-focus position is away from the previous position by more than the predetermined moving amount W on the +side. This situation will not occur in the case of photographing the same eye. Hence, the focusing lens 15 is moved by W from the start position 301 to the − side, and the threshold value L1 is updated to start scanning S1.

After detection of a peak of a focusing evaluation value curve, a value obtained by subtracting the threshold value L1 set in the start position of the scanning S1 from the peak value is set to h. If the value h is larger than a reference value, the threshold value L1 is updated to a value lower than the peak value by a half of the value h (h/2) from the peak value. When the scanning is continued, and a focusing evaluation value drops below the threshold value L1, the scanning is stopped, and the focusing lens 15 is moved (M2) to the peak position.

Figure 7:
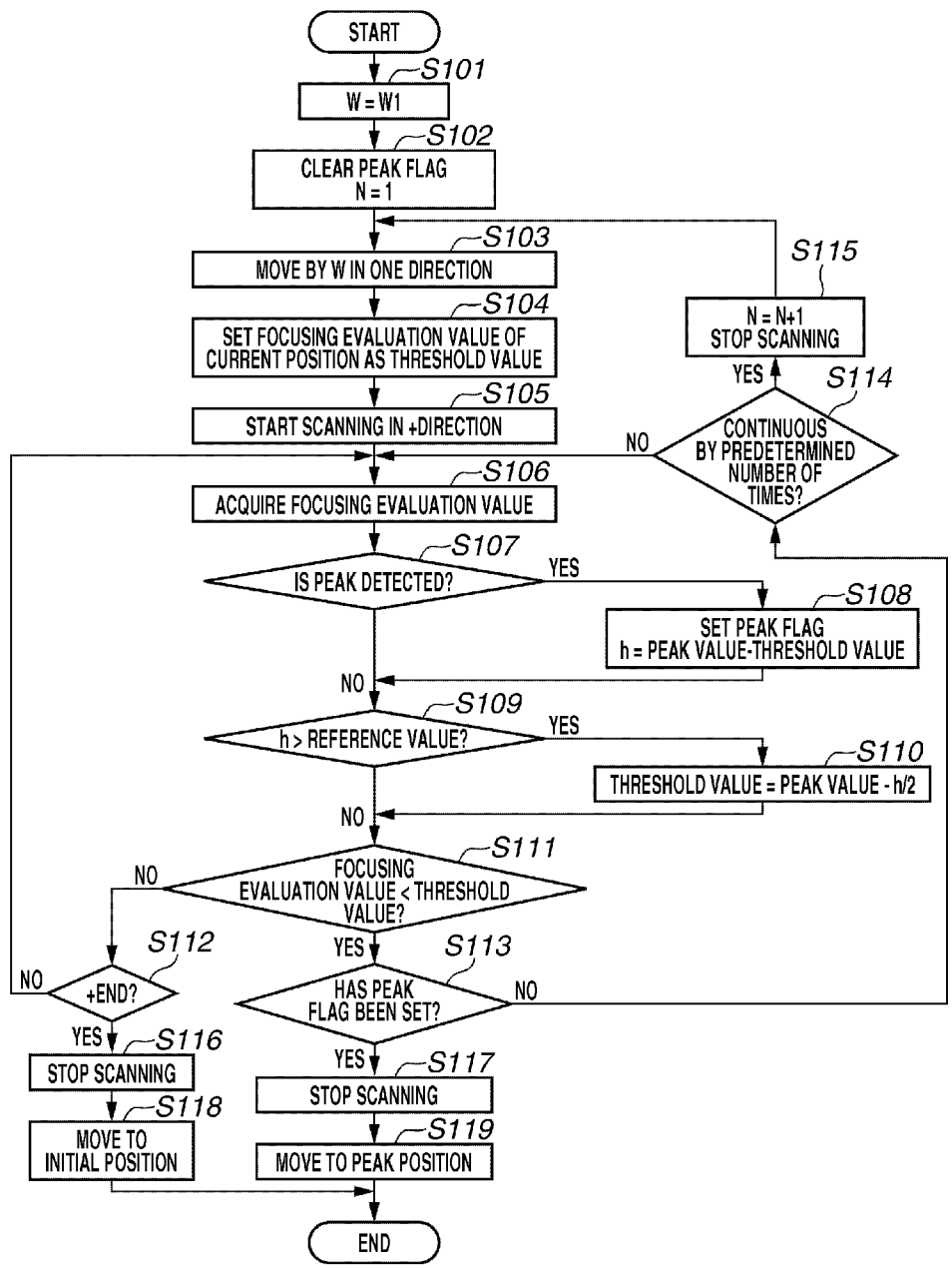
FIG. 7 is a flowchart illustrating an operation of the focusing lens.

FIG. 7 is a flowchart illustrating the operations of FIGS. 3 to 6.

First, in a focusing routine, in step S101, a moving amount W1 is set to a predetermined moving amount W. In step S102, a flag for storing presence of a peak is cleared, and the number of moving times N is set to 1. In step s103, the focusing lens 15 is moved in the "−" direction by W. When exceeding the − end, the focusing lens 15 is moved to the − end. In step S104, a focusing evaluation value in a position to which the focusing lens 15 has been moved is acquired and set as a threshold value.

In step S105, scanning is started in the + end direction. In step S106, a focusing evaluation value is acquired. In step S107, presence of a detected peak is determined. In peak determination, a shape such as an increase by a predetermined moving amount, a decrease by a predetermined moving amount, or a certain width is checked.

If there is a peak (YES in step S107), the processing proceeds to step S108. In step S108, a peak flag is set, and a value obtained by subtracting the focusing evaluation value acquired at the start of the focusing scanning S1 from the peak value of the focusing evaluation value is set as the value h. In step S109, the value h is compared with a reference value. If the value h is larger than the reference value (YES in step S109), the processing proceeds to step S110. In step S110, the threshold value L1 is set to a value obtained by subtracting h/2 from the peak value.

In step S111, a current focusing evaluation value is compared with the threshold value L1. If the current focusing evaluation value is smaller than the threshold value L1 (YES in step S111), the processing proceeds to step S113. If larger (NO in step S111), the processing proceeds to step S112. In step S112, whether the + end has been reached is determined. If the + end has not been reached (No in step S112), the processing is repeated from step S106. If the + end has been reached (YES in step S112), the processing proceeds to step S116. In step S116, the scanning is stopped. In step S118, the focusing lens 15 is moved to the initial position.

A normal initial position is a 0 diopter position. In this case, the examiner is notified of non-detection of an in-focus position by a display (not illustrated). In step S113, a peak flag is determined. If a peak has been detected (YES in step S113), the processing proceeds to step S117. In step S117, the scanning is stopped. If no peak has been detected (NO in step S113), the processing proceeds to step S114.

In step S114, whether focusing evaluation values are continuously lower than the threshold value L1 is determined. If the focusing evaluation values are continuously equal to or less than the threshold value L1 (YES in step S114), in step S115, the scanning is stopped. The number of moving times N is counted up to repeat the processing from step S103.

If the focusing evaluation values are not continuously equal to or less than the threshold value L1 (NO in step S114), the processing is repeated from step S106.

The proceeding proceeds from step S117 to step S119, a curve of the acquired focusing evaluation values is complemented by a spline curve, a curve of the focusing evaluation values is calculated, and the focusing lens 15 is moved to a vertex position of a mountain to finish the focusing routine. When the focusing is normally completed, the examiner may be notified of the completion by a display (not illustrated).

Figure 8:
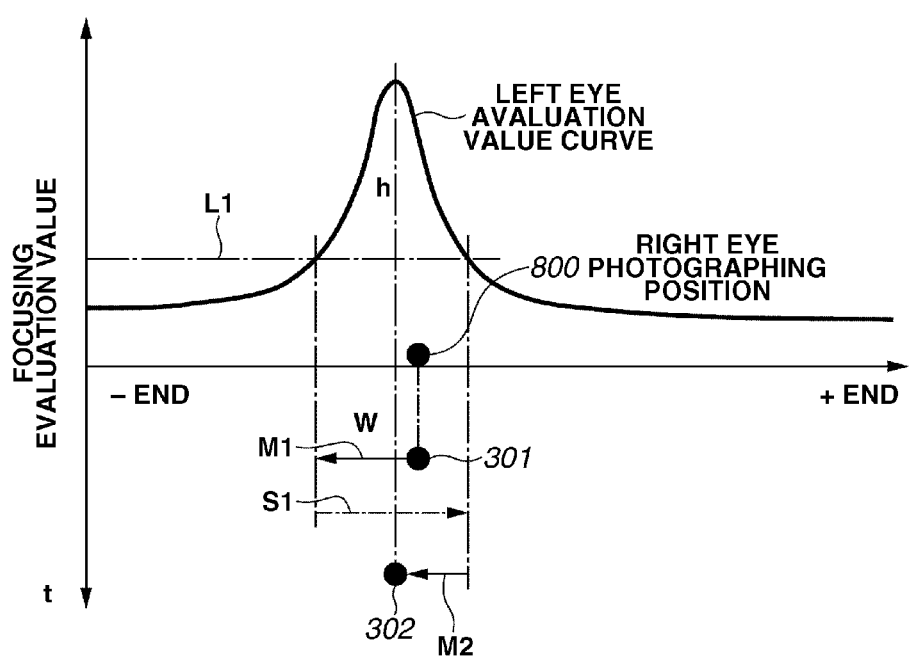
FIG. 8 is a graph illustrating an operation of the focusing lens.

FIG. 8 illustrates an example of photographing performed by switching to the other eye after one eye of the same subject is photographed.

After switching of a photographing eye, an ON/OFF signal of the left/right eye detection unit 34 is input to the control unit 31, and switching of the left and right eyes is determined. For example, when photographing of the right eye is finished to switch to the left eye, the focusing lens 15 is moved by a predetermined moving amount W from a right eye photographing position 800 in the −end direction. When the shooting switch 35 is pressed half, focusing scanning S1 is started.

A peak is detected, and the focusing lens 15 is moved (M2) to the peak position to complete focusing.

When the examiner recognizes the focusing by a display or a sound (not illustrated), and fully presses the shooting switch 35 after checking of a photographing portion, the flash light source 6 emits light to perform fundus photographing. In the case of this operation, if the focusing driving system can move the focusing lens 15 at a high speed, the focusing lens 15 may be moved by the predetermined moving amount W after the shooting switch 35 is pressed half.

Figure 9:
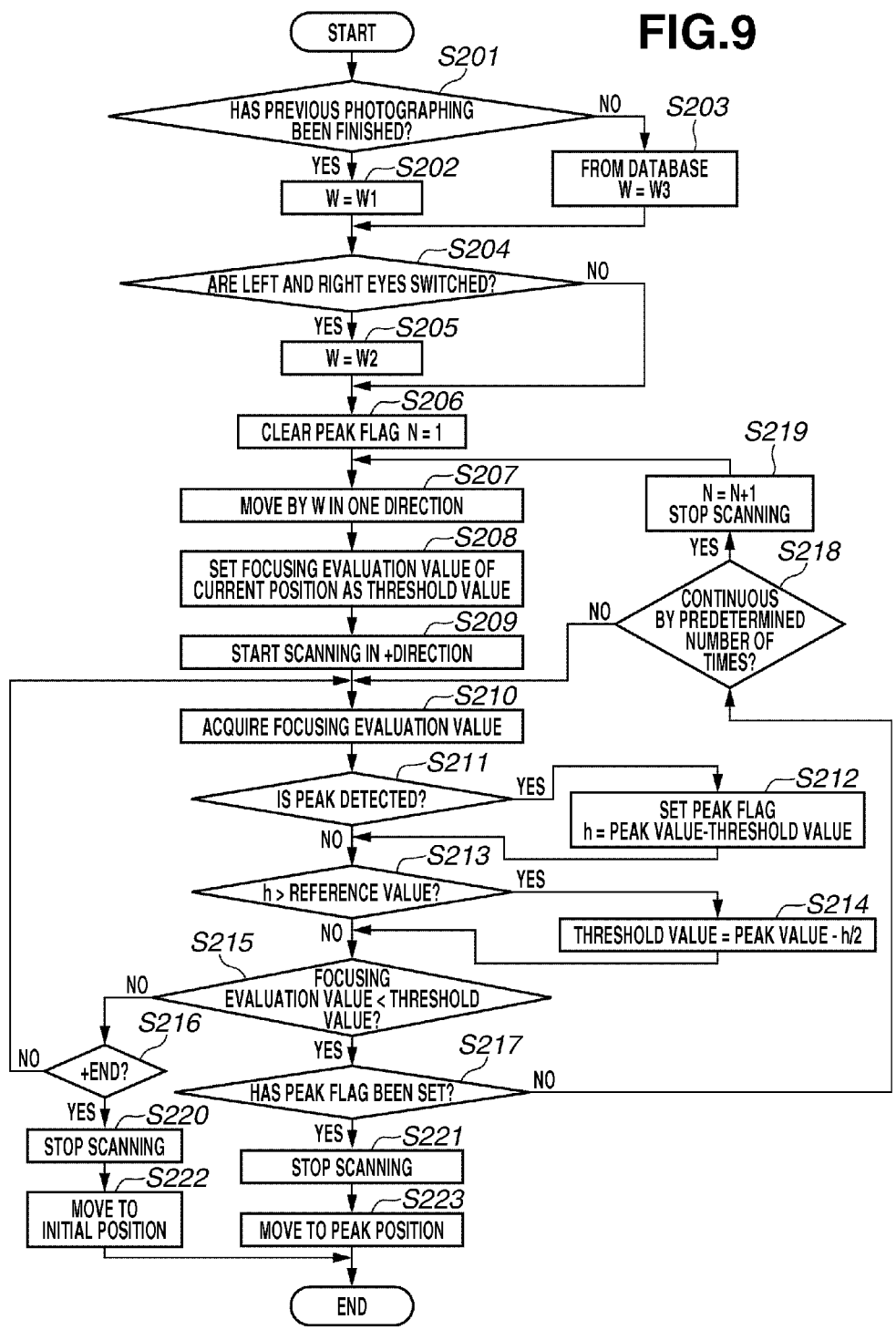
FIG. 9 is a flowchart illustrating an operation of the focusing lens.
Figure 10:
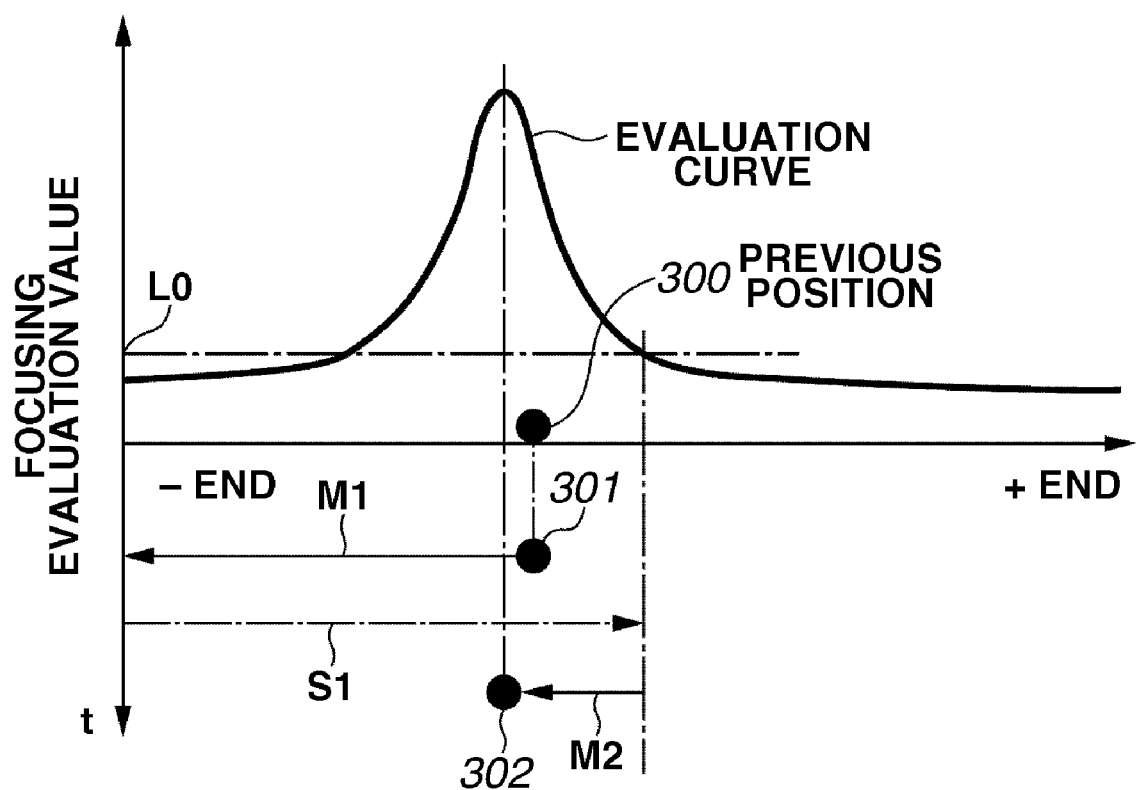
FIG. 10 is a graph illustrating an operation of a conventional focusing lens.

FIG. 9 is a flowchart illustrating processing that includes checking of the presence of previous photographing and the left/right eye switching as illustrated in FIG. 8.

First, in step S201, completion of previous photographing is determined based on whether photographing of the same eye has been performed within a predetermined period of time. If more than the predetermined period of time has passed, the previous photographing is determined as uncompleted. If completed (YES in step S201), in step S202, the moving amount W1 is set as the predetermined moving amount W. If uncompleted (NO in step S201), in step S203, a moving amount W3 is set in the predetermined moving amount W. In step S204, whether switching has been made to the other eye is determined. If switched (YES in step S204), then in step S205, a moving amount W2 is set in the predetermined moving amount W.

If the same eye is repeatedly photographed, no change occurs more than one diopter or more even including a fluctuation due to adjustment, a change due to a photographing position, and a change in positional relationship with the fundus camera. A value obtained by adding a half-value width of a focusing evaluation value curve to this diopter is set as a moving amount W1. A refractive power difference between the left and right eyes is within 1 to 1.5 diopters, and a value obtained by adding the half-value width of the focusing evaluation value curve to a corresponding amount is set as a moving amount W2.

A photographing position distribution of the focusing lens 15 photographed in a current shooting mode within an immediate one month from the database of the storage unit 32 is considered as a normal distribution, and a value obtained by adding the half-value width of the focusing evaluation value curve to standard deviation from the center position is set as a moving amount W3. When the number of data for statistical processing is small, a range is sequentially widened from one month, and sizes of moving amounts accordingly take larger values in order of W1<W2<W3. Processing of step S207 and subsequent steps is similar to step S103 of FIG. 7.

In the flowcharts of FIGS. 7 and 9, the focusing routine includes the first moving position of the focusing lens 15. The inclusion of this position is not such a big problem when a moving speed of the driving system of the focusing lens 15 is sufficiently high. If the moving speed is not sufficiently high, however, the focusing lens 15 is moved beforehand when the left and right eyes are switched.

Similarly, when the same eye is repeatedly photographed, the focusing lens 15 is moved (M2) immediately after photographing, and next photographing is started from scanning S1. In the case of performing the first movement M1 separately from and before the focusing routine, when the number of moving times N is initialized in each flowchart, N=2 only needs to be set.

When values of the moving amounts W1, W2, and W3 used to set the predetermined moving amount are small, a moving period of time and a scanning period of time can be reduced. Thus, to match an environment where the fundus camera is used, the values are updated by reading from the database as necessary.

In the description of the flowchart, the moving direction is the − side, and the scanning for focusing value acquisition is moved in the + direction. However, directions may be reverse.

According to the fundus camera of the exemplary embodiment of the present invention, performing focusing evaluation value scanning after movement by a predetermined moving amount enables shortening of a period of time until focusing completion. The fundus camera of the exemplary embodiment is advantageous in that not only efficiency of fundus photographing can be improved but also loads on the subject can be reduced. Moreover, setting a predetermined moving amount to an appropriate value according to a situation enables efficient focusing control.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-113451 filed May 8, 2009, which is hereby incorporated by reference herein in its entirety.

What is claimed is:

1. A fundus camera comprising:
    an observation photographing unit having a focusing lens to perform focusing of an imaging unit on a fundus of a subject's eye;
    a lens driving unit configured to drive the focusing lens in an optical axis direction; and
    a focusing control unit configured to calculate a focusing evaluation value based on image information of a predetermined area of a fundus image captured by the observation photographing unit, and drive the focusing lens based on the focusing evaluation value, thereby performing focusing,
    wherein the focusing control unit moves the focusing lens from a previous photographing position of the focusing lens by a predetermined moving amount, and then performs the focusing.

2. The fundus camera according to claim 1, further comprising a left/right eye detection unit configured to detect whether the subject's eye to be photographed is left or right,
    wherein when the left/right eye detection unit detects an eye different from the eye to be photographed, the focusing control unit moves a position of the focusing lens by a predetermined moving amount, and then performs the focusing.

3. The fundus camera according to claim 2, wherein when a predetermined period of time has passed after previous photographing, the predetermined moving amount is increased.

4. The fundus camera according to claim 2, wherein when the left/right eye detection unit detects another side of the subject's eye and the other eye is yet to be photographed, the predetermined moving amount is increased.

5. The fundus camera according to claim 1, wherein the focusing control unit includes a storage unit configured to store a focusing position for each photographing, and determines the predetermined moving amount based on a photographing position distribution stored in the storage unit.

* * * * *